US 9,389,161 B2

(12) United States Patent
Reimers

(10) Patent No.: US 9,389,161 B2
(45) Date of Patent: Jul. 12, 2016

(54) ON-LINE FT-NIR METHOD TO DETERMINE PARTICLE SIZE AND DISTRIBUTION

(71) Applicant: ExxonMobil Chemical Patents Inc., Baytown, TX (US)

(72) Inventor: Jay L. Reimers, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/639,258

(22) Filed: Mar. 5, 2015

(65) Prior Publication Data
US 2015/0293005 A1 Oct. 15, 2015

Related U.S. Application Data

(60) Provisional application No. 61/977,420, filed on Apr. 9, 2014.

(51) Int. Cl.
*G01N 21/35* (2014.01)
*G01J 3/44* (2006.01)
*G01J 3/45* (2006.01)
*G01N 15/02* (2006.01)

(52) U.S. Cl.
CPC .............. *G01N 15/0205* (2013.01); *G01J 3/45* (2013.01); *G01N 21/35* (2013.01)

(58) Field of Classification Search
CPC .......... G01J 3/44; G01J 3/35; G01N 15/0205; G01N 21/35
See application file for complete search history.

(56) References Cited

U.S. PATENT DOCUMENTS

| 4,243,619 A | 1/1981 | Fraser et al. |
| 4,543,399 A | 9/1985 | Jenkins, III et al. |

(Continued)

FOREIGN PATENT DOCUMENTS

| EP | 561 078 | 10/1992 |
| WO | 98/08066 | 8/1996 |

(Continued)

OTHER PUBLICATIONS

O'Neil et al., "Measurement of the percentage volume particle size distribution of powdered microcrystalline cellulose using reflectance near-infrared spectroscopy," Analyst, 2003, vol. 128(11), pp. 1326-1330.

(Continued)

*Primary Examiner* — David Porta
*Assistant Examiner* — Faye Boosalis

(57) ABSTRACT

This invention relates to a method for the determination of the average particle size or particle size distribution of a material in a gas phase reactor comprising: 1) analyzing the average particle size and particle size distribution of a baseline composition using the method described in ASTM D1921; 2) analyzing the average particle size and particle size distribution of said baseline composition using an FT-NIR analysis technique; 3) preparing a calibration matrix by comparing results from said reference analytical technique to the results from said FT-NIR analysis technique; 4) analyzing the material using an FT-NIR technique; and 5) identifying and quantifying the type and content of particles present in the material by comparing spectral data obtained from said FT-NIR technique of the material to said calibration matrix.
This invention also relates to a process for determining polymer properties in a polymerization reactor system using such techniques.

24 Claims, 6 Drawing Sheets

(56) References Cited

U.S. PATENT DOCUMENTS

| | | |
|---|---|---|
| 4,588,790 A | 5/1986 | Jenkins, III et al. |
| 5,151,474 A | 9/1992 | Lange et al. |
| 5,352,749 A | 10/1994 | DeChellis et al. |
| 5,405,922 A | 4/1995 | DeChellis et al. |
| 5,436,304 A | 7/1995 | Griffin et al. |
| 5,462,999 A | 10/1995 | Griffin et al. |
| 5,999,255 A | 12/1999 | Dupée et al. |
| 6,144,897 A | 11/2000 | Selliers |
| 6,218,484 B1 | 4/2001 | Brown et al. |
| 6,864,331 B1 | 3/2005 | Reimers et al. |
| 7,116,414 B2 | 10/2006 | Long et al. |
| 7,329,547 B2 | 2/2008 | Azizian |
| 2005/0250212 A1 | 11/2005 | Azizian |

FOREIGN PATENT DOCUMENTS

| | | |
|---|---|---|
| WO | 01/09201 | 2/2001 |
| WO | 01/09203 | 2/2001 |
| WO | 02/054061 | 7/2002 |
| WO | 2005/005965 | 1/2005 |
| WO | 2005/049663 | 6/2005 |

OTHER PUBLICATIONS

Ardell, G.G. et al., "*Model Prediction for Rreactor Control*," Chemical Engineering Progress, American Institute of Chemical Engineers, (ISSN 0360-7275), 1983, vol. 79(6), pp. 77-83.

Chicoma et al., "*In-Line Monitoring of Particle Size during Emulsion Polymerization under Different Operational Conditions using NIR Spectroscopy*," Macromolecular Reaction Engineering, 2011, vol. 5(3-4), pp. 150-162.

Pater et al., "*New Method for Online Observation of Growing Polyolefin Particles*," Chimia, 2001, vol. 55(3), pp. 231-233.

Ito et al., "*Non-destructive method for the quantification of the average particle diameter of latex as water-based emulsions by near-infrared Fourier transform Raman spectroscopy*," Journal of Raman Spectroscopy, vol. 33(6), 2002, pp. 466-470.

Liana et al., "*Analysis of Polyolefin Compositions Through Near Infrared Spectroscopy*," Journal of Applied Polymer Science, 2013, vol. 131(9), pp. 1-13.

Silva et al., "*In-Situ Real-Time Monitoring of Particle Size, Polymer, and Monomer Contents in Emulsion Polymerization of Methyl Methacrylate by Near Infrared Spectroscopy*," Polymer Engineering and Science, 2011, vol. 51(10), pp. 2024-2034.

Santos et al., "*Control and Design of Average Particle Size in Styrene Suspension polymerizations using NIRS*," Journal of Applied Polymer Science, vol. 77(2), 2000, pp. 453-462.

Santos et al., "*Monitoring and Control of Polymerization Reactors using NIR Spectroscopy*," Polymer Plastics Technology and Engineering, NY, NY, vol. 44(1), 2006, pp. 1-61.

Strother, Todd, Technical Note: 51768, *NIR and RAMAN: Complementary Techniques for Raw Material Identification*, Thermo Fisher Scientific, Madison, Wi, USA, 2009.

ON-LINE FT-NIR METHOD TO DETERMINE PARTICLE SIZE AND DISTRIBUTION

CROSS-REFERENCE TO RELATED APPLICATIONS

This application claims priority to and the benefit of application of U.S. Provisional Application Ser. No. 61/977,420, filed Apr. 9, 2014, the entirety of which is incorporated herein by reference.

FIELD OF THE INVENTION

This invention relates to Fourier Transform Near-Infrared spectrophotometry and its use to determine particle size and particle size distribution of polymer particles, particularly in a gas phase reactor, and in particular, using those measured properties to control the polymerization reaction in a gas phase reactor. The present invention provides methods of measuring properties of polyolefins such as particle size and particle size distribution on-line, using FT-NIR, and methods of controlling a reactor using real-time, on-line polymer property data provided by the FT-NIR measurements.

BACKGROUND

Gas phase processes for the homopolymerization and copolymerization of monomers, especially olefin monomers, are known in the art and are typically conducted, for example, by introducing the gaseous monomer or monomers into a stirred and/or fluidized bed of resin particles and catalyst. In a fluidized-bed polymerization of olefins, the polymerization is conducted in a fluidized-bed reactor, wherein a bed of polymer particles is maintained in a fluidized state by means of an ascending gas stream including gaseous reaction monomer. The polymerization of olefins in a stirred-bed reactor differs from polymerization in a gas fluidized-bed reactor by the action of a mechanical stirrer within the reaction zone, which contributes to fluidization of the bed. As used herein, the term "fluidized-bed" also includes stirred-bed processes and reactors.

During the course of polymerization, fresh polymer is generated by the catalytic polymerization of the monomer, and polymer product is withdrawn to maintain the bed at constant volume. An industrially favored process employs a fluidization grid to distribute the fluidizing gas to the bed, and also to act as a support for the bed when the supply of gas is cut off. The polymer produced is generally withdrawn from the reactor via one or more discharge conduits disposed in the lower portion of the reactor, near the fluidization grid. The fluidized bed includes a bed of growing polymer particles, polymer product particles and catalyst particles. This reaction mixture is maintained in a fluidized condition by the continuous upward flow from the base of the reactor of a fluidizing gas which includes recycle gas drawn from the top of the reactor, together with added make-up monomer. The fluidizing gas enters the bottom of the reactor and is passed, preferably through a fluidization grid, upwardly through the fluidized bed.

The polymerization of olefins is an exothermic reaction, and it is therefore necessary to cool the bed to remove the heat of polymerization. In the absence of such cooling, the bed would increase in temperature until, for example, the catalyst became inactive or the polymer particles melted and began to fuse, causing fouling. In the fluidized-bed polymerization of olefins, a typical method for removing the heat of polymerization is by passing a cooling gas, such as the fluidizing gas, which is at a temperature lower than the desired polymerization temperature, through the fluidized-bed to conduct away the heat of polymerization. The gas is removed from the reactor, cooled by passage through an external heat exchanger and then recycled to the bed. The temperature of the recycle gas can be adjusted in the heat exchanger to maintain the fluidized-bed at the desired polymerization temperature. In this method of polymerizing alpha olefins, the recycle gas generally includes one or more monomeric olefins, optionally together with, for example, an inert diluent gas or a gaseous chain transfer agent such as hydrogen. The recycle gas thus serves to supply monomer to the bed to fluidize the bed and to maintain the bed within a desired temperature range. Monomers consumed by conversion into polymer in the course of the polymerization reaction are normally replaced by adding make-up monomer to the recycle gas stream.

The polymerization process can use Ziegler-Natta and/or metallocene catalysts. A variety of gas phase polymerization processes are known. For example, the recycle stream can be cooled to a temperature below the dew point, resulting in condensing a portion of the recycle stream, as described in U.S. Pat. Nos. 4,543,399 and 4,588,790. This intentional introduction of a liquid into a recycle stream or reactor during the process is referred to generally as a "condensed mode" operation. Further details of fluidized bed reactors and their operation are disclosed in, for example, U.S. Pat. Nos. 4,243,619, 4,543,399, 5,352,749, 5,436,304, 5,405,922, 5,462,999, and 6,218,484, the disclosures of which are incorporated herein by reference.

The properties of the polymer produced in the reactor are affected by a variety of operating parameters, such as temperatures, monomer feed rates, catalyst feed rates, particle size and hydrogen gas concentration. In order to produce polymer having a desired set of properties, such as melt index and density, polymer exiting the reactor is sampled and laboratory measurements carried out to characterize the polymer. If it is discovered that one or more polymer properties are outside a desired range, polymerization conditions can be adjusted, and the polymer resampled. This periodic sampling, testing and adjusting, however, is undesirably slow, since sampling and laboratory testing of polymer properties such as melt index, molecular weight distribution, average particle size, particle size distribution, and/or density is time-consuming. As a result, conventional processes can produce large quantities of "off-spec" polymer before manual testing and control can effectively adjust the polymerization conditions. This occurs during production of a particular grade of resin as well as during the transition process between grades.

Methods have been developed to attempt to provide rapid assessment of certain polymer properties and rapid adjustment of polymerization conditions. U.S. Pat. No. 7,116,414 discloses a method of on-line monitoring using Raman based methods. PCT publications WO 2001/09201 and WO 2001/09203 disclose Raman-based methods using principal components analysis (PCA) and partial least squares (PLS) to determine concentrations of components in a slurry reactor. The concentration of a particular component, such as ethylene or hexene, is determined based on measurements of a known Raman peak corresponding to the component. U.S. Pat. No. 5,999,255 discloses a method for measuring a physical property of a polymer sample, preferably nylon, by measuring a portion of a Raman spectrum of the polymer sample, determining a value of a preselected spectral feature from the Raman spectrum, and comparing the determined value to reference values. WO 2005/049663 discloses on-line measurement and control of polymer properties using Raman spectroscopy in a fluidized bed reactor.

Additional background information can be found in U.S. Pat. Nos. 6,144,897 and 5,151,474; European Patent application EP 0 561 078; PCT publication WO 98/08066; and Ardell, G. G. et al., "Model Prediction for Reactor Control," *Chemical Engineering Progress*, American Institute of Chemical Engineers, U.S., vol. 79, no. 6, Jun. 1, 1983, pages 77-83 (ISSN 0360-7275).

It would also be desirable to have methods of controlling a gas-phase fluidized bed reactor to maintain desired polymer properties, based on a rapid, on-line determination of the polymer properties, such as average particle size and particle size distribution.

The average particle size and particle size distribution of polymer particles formed in a gas phase reactor are known to affect the performance and robustness of the process. Smaller particles contribute to detrimental polymer carry-over into the recycle system and static charges within the reactor. In addition particle size serves as indirect measure catalyst productivity. Therefore, measuring the particle size in general is useful in monitoring and controlling the performance of a gas phase reactor. A method that affords an indication of particle size in real-time and in-situ has the added benefits of a faster response time and no sample preparation. The current method of particle size measurement relies on reactor sampling and offline sieve analysis which results in a time lag, and therefore a potential difference, between what the process is actually producing and what is measured.

WO 2002/054061 discloses a method for determining flour baking properties using near infrared (NIR).

WO 2005/005965 discloses the use of a non-Gaussian laser beam to measure particle size and particle concentration in dilute media.

*Analyst*, 2003, 128 (11), 1326-1330 discloses a method for determining percentage volume particle size distribution of powdered microcrystalline cellulose.

U.S. Pat. No. 6,864,331 discloses a polymerization process where a sensor probe connected to a near-IR spectrophotometer light source connected by a fiber optic cable is used to measure a polymer characteristic. The value for the characteristic is a component of an algorithm and the algorithm is used, in real time, to monitor and/or control the process for preparing a polymer. U.S. Pat. No. 6,864,331 focuses on slurry processes and the settling legs on a loop reactor.

WO 2005/005965 discloses the use of a non-Gaussian laser beam to measure particle size and particle concentration in dilute media.

Macromolecular Reaction Engineering (2011), 5(3-4), 150-162 discloses the use of NIR to track the evolution of particle growth during the emulsion polymerization of styrene.

Polymer Engineering and Science (2011), 51(10), 2014 2024-2034 discloses the use of NIR for the in-situ, real-time monitoring of the emulsion polymerization of methyl methacrylate.

Chimia (2001), 55(3), pg 231-233 discloses a method for direct observation of growing polymer particles in a gas phase polymerization cell with a transparent lid using IR.

Additional references of interest include: U.S. Pat. No. 7,329,547.

SUMMARY OF THE INVENTION

This invention relates to a method for the determination of the average particle size or particle size distribution of a material in a gas phase reactor comprising:

a) analyzing the average particle size and particle size distribution of a baseline composition using the method described in ASTM D1921;
b) analyzing the average particle size and particle size distribution of said baseline composition using a Fourier Transform-Near Infrared, FT-NIR, analysis technique;
c) preparing a calibration matrix by comparing results from said reference analytical technique of step as to the results from said FT-NIR analysis technique of step b);
d) analyzing the material using an FT-NIR technique; and
e) identifying and quantifying the type and content of particles present in the material by comparing spectral data obtained from said FT-NIR technique of the material to said calibration matrix.

This invention also relates to a process for determining polymer properties in a polymerization reactor system, the process comprising:

(a) obtaining a regression model for determining a polymer property, the regression model including principal component loadings and principal component scores;
(b) acquiring a FT-NIR spectrum of a sample comprising polyolefin;
(c) calculating a new principal component score from at least a portion of the FT-NIR spectrum and the principal component loadings; and
(d) calculating the polymer property by applying the new principal component score to the regression model.

DETAILED DESCRIPTION

In one embodiment, the present invention provides a method of determining polyolefin polymer particle properties on-line, i.e., as the polyolefin is produced in a reactor system, without the need for external sampling and analysis. The method includes obtaining a regression model for determining a polymer property, the regression model including principal component loadings and principal component scores, acquiring a FT-NIR spectrum of a polyolefin sample, calculating a new principal component score from at least a portion of the FT-NIR spectrum and the principal component loadings, and calculating the polymer property by applying the new principal component score to the regression model.

In one embodiment, the method is used to determine polymer particle properties on-line in a fluidized-bed reactor system. Fluidized-bed reactors are well-known in the art; a particular, non-limiting example of a fluidized bed reactor is described herein, for illustrative purposes only. Those skilled in the art will recognize that numerous modifications and enhancements can be made, as desired, to the fluidized-bed reactor as described below.

This invention relates to an in-situ means of measuring the average particle size and particle size distribution of polymer granules made in a gas phase reactor, and in particular, relates to an on-line in-situ means of measuring the average particle size and particle size distribution of polymer granules made in a gas phase reactor in real-time. The method uses online Fourier Transform Near-Infrared (FT-NIR) spectrophotometry, and by comparing the measured spectra to spectra from known particle size distributions, the average particle size and particle size distribution of the polymer granules being made in the reactor can be inferred in real-time. The advantage of the method is a continuous indication of average particle size and particle size distribution.

Fluidized-Bed Reactor

Figure 1:
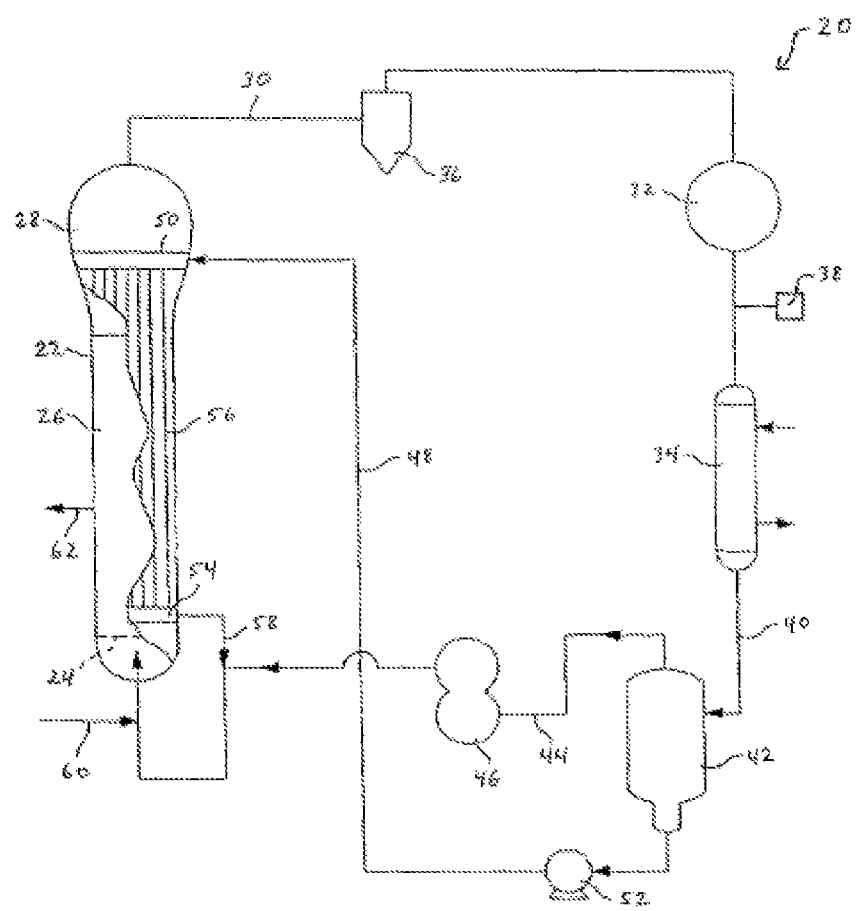
FIG. 1 is a block diagram of a gas-phase reactor.

FIG. 1 illustrates a gas-phase fluidized bed reactor 20 having a reactor body 22, which is generally an upright cylinder having a fluidization grid 24 located in its lower regions. The reactor body 22 encloses a fluidized bed zone 26 and a velocity reduction zone 28 which is generally of increased diameter compared to the diameter of the fluidized bed zone 26 of the reactor body 22.

The gaseous reaction mixture leaving the top of the reactor body 22, termed the "recycle gas stream," contains principally unreacted monomer, unreacted hydrogen gas, inert condensable gases such as isopentane, and inert non-condensable gases such as nitrogen. The recycle gas stream is transferred via line 30 to compressor 32, and from compressor 32 to heat exchanger 34. An optional cyclone separator 36 may be used as shown, preferably upstream of compressor 32, to remove fines, if desired. An optional gas analyzer 38 can be used if desired, to sample the recycle gas stream to determine concentrations of various components. Typically, the gas analyzer is a gas phase chromatograph (GPC), or a spectrograph such as a near-infrared spectrometer or a fourier transform near-infrared spectrometer (FT-NIR). An additional heat exchanger (not shown) may also be used if desired, preferably upstream of compressor 32.

The cooled recycle gas stream exits the heat exchanger 34 via line 40. As discussed above, the cooled recycle gas stream can be gaseous, or can be a mixture of gaseous and liquid phases. FIG. 1 shows an optional configuration wherein at least a portion of the recycle gas stream is cooled to a temperature at or below the temperature where liquid condensate begins to form (the dew point). All or a portion of the resultant gas liquid mixture is transferred via line 40 to a separator 42, where all or a portion of the liquid is removed. All or a portion of the gas stream, which may contain some liquid, is transferred via line 44 to a point below the fluidization grid 24 in the lower region of the reactor. An amount of upwardly flowing gas, sufficient to maintain the bed in a fluidized condition, is provided in this way.

Those skilled in the art will understand that less gas is required to maintain fluidization when the reactor employed is a stirred bed reactor.

An optional compressor 46 may be provided to ensure that a sufficient velocity is imparted to the gases flowing through line 44 into the bottom of the reactor. The gas stream entering the bottom of the reactor may contain condensed liquid, if desired.

All or a portion of the liquid phase separated from the recycle stream in separator 42 is transferred via line 48 to a manifold 50 located at or near the top of the reactor. If desired, a pump 52 may be provided in line 48 to facilitate the transfer of liquid to manifold 50. The liquid entering manifold 50 flows downward into manifold 54 through a plurality of conduits 56 which have good heat exchange properties and which are in heat exchange contact with the wall of the reactor. The passage of liquid through the conduits 56 cools the interior wall of the reactor and warms the liquid to a greater or lesser extent, depending upon the temperature differential and the duration and extent of heat exchange contact. Thus by the time the liquid entering manifold 50 reaches manifold 54, it has become a heated fluid which may have remained in an entirely liquid state or it may have become partially or totally vaporized.

As shown in FIG. 1, the heated fluid (gas and/or liquid) is passed from manifold 54 via line 58 to combine with gases leaving the separator 42 via line 44, prior to entry into the reactor in the region below the fluidization grid 24. In like manner, make-up monomer can be introduced into the reactor in either liquid or gaseous form via line 60. Gas and/or liquid collected in manifold 54 may also be transferred directly into the reactor (not shown) in the region below the fluidization grid.

Product polymer particles can be removed from the reactor via line 62 in the conventional way, as for example by the method and apparatus described in U.S. Pat. No. 4,621,952. Although only one line 62 is shown in the Figure, typical reactors can include more than one line 62.

Catalyst is continuously or intermittently injected into the reactor using a catalyst feeder (not shown) such as the device disclosed in U.S. Pat. No. 3,779,712. The catalyst is preferably fed into the reactor at a point 20 to 40 percent of the reactor diameter away from the reactor wall and at a height of about 5 to about 30 percent of the height of the bed. The catalyst can be any catalyst suitable for use in a fluidized bed reactor and capable of polymerizing ethylene, such as one or more metallocene catalysts, one or more Ziegler-Natta catalysts, bimetallic catalysts, or mixtures of catalysts.

A gas which is inert to the catalyst, such as nitrogen or argon, is preferably used to carry catalyst into the bed. Cold condensed liquid from either separator 42 or from manifold 54 may also be used to transport catalyst into the bed.

In methods of the present invention, the fluidized bed reactor is operated to form at least one polyolefin homopolymer or copolymer. Suitable polyolefins include, but are not limited to, polyethylene, polypropylene, polyisobutylene, and homopolymers and copolymers thereof.

In one embodiment, the at least one polyolefin includes polyethylene homopolymer and/or copolymer. Low density polyethylene ("LDPE") can be prepared at high pressure using free radical initiators, or in gas phase processes using Ziegler-Natta or vanadium catalysts, and typically has a density in the range of 0.916-0.940 g/cm$^3$. LDPE is also known as "branched" or "heterogeneously branched" polyethylene because of the relatively large number of long chain branches extending from the main polymer backbone. Polyethylene in the same density range, i.e., 0.916 to 0.940 g/cm$^3$, which is linear and does not contain long chain branching is also known; this "linear low density polyethylene" ("LLDPE") can be produced with conventional Ziegler-Natta catalysts or with metallocene catalysts. Polyethylenes having still greater density are the high density polyethylenes ("HDPEs"), i.e., polyethylenes having densities greater than 0.940 g/cm$^3$, and are generally prepared with Ziegler-Natta catalysts. Very low density polyethylene ("VLDPE") is also known. VLDPEs can be produced by a number of different processes yielding polymers with different properties, but can be generally described as polyethylenes having a density less than 0.916 g/cm$^3$, typically 0.890 to 0.915 g/cm$^3$ or 0.900 to 0.915 g/cm$^3$.

Polymers having more than two types of monomers, such as terpolymers, are also included within the term "copolymer" as used herein. Suitable comonomers include α-olefins, such as $C_3$-$C_{20}$ α-olefins or $C_3$-$C_{12}$ α-olefins. The α-olefin comonomer can be linear or branched, and two or more comonomers can be used, if desired. Examples of suitable comonomers include linear $C_3$-$C_{12}$ α-olefins, and α-olefins having one or more $C_1$-$C_3$ alkyl branches, or an aryl group. Specific examples include propylene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. It should be appreciated that the list of comonomers above is merely exemplary, and is not intended to be limiting. Preferred comonomers include propylene, 1-butene, 1-pentene, 4-methyl-1-pentene, 1-hexene, 1-octene and styrene.

Other useful comonomers include polar vinyl, conjugated and non-conjugated dienes, acetylene and aldehyde monomers, which can be included in minor amounts in terpolymer compositions. Non-conjugated dienes useful as co-monomers preferably are straight chain, hydrocarbon diolefins or cycloalkenyl-substituted alkenes, having 6 to 15 carbon atoms. Suitable non-conjugated dienes include, for example: (a) straight chain acyclic dienes, such as 1,4-hexadiene and 1,6-octadiene; (b) branched chain acyclic dienes, such as 5-methyl-1,4-hexadiene; 3,7-dimethyl-1,6-octadiene; and 3,7-dimethyl-1,7-octadiene; (c) single ring alicyclic dienes, such as 1,4-cyclohexadiene; 1,5-cyclo-octadiene and 1,7-cyclododecadiene; (d) multi-ring alicyclic fused and bridged ring dienes, such as tetrahydroindene; norbornadiene; methyl-tetrahydroindene; dicyclopentadiene (DCPD); bicyclo-(2.2.1)-hepta-2,5-diene; alkenyl, alkylidene, cycloalkenyl and cycloalkylidene norbornenes, such as 5-methylene-2-norbornene (MNB), 5-propenyl-2-norbornene, 5-isopropylidene-2-norbornene, 5-(4-cyclopentenyl)-2-norbornene, 5-cyclohexylidene-2-norbornene, and 5-vinyl-2-norbornene (VNB); and (e) cycloalkenyl-substituted alkenes, such as vinyl cyclohexene, allyl cyclohexene, vinyl cyclooctene, 4-vinyl cyclohexene, allyl cyclodecene, and vinyl cyclododecene. Of the non-conjugated dienes typically used, the preferred dienes are dicyclopentadiene, 1,4-hexadiene, 5-methylene-2-norbornene, 5-ethylidene-2-norbornene, and tetracyclo-(Δ-11,12)-5,8-dodecene. Particularly preferred diolefins are 5-ethylidene-2-norbornene (ENB), 1,4-hexadiene, dicyclopentadiene (DCPD), norbornadiene, and 5-vinyl-2-norbornene (VNB).

The amount of comonomer used will depend upon the desired density of the polyolefin and the specific comonomers selected. One skilled in the art can readily determine the appropriate comonomer content appropriate to produce a polyolefin having a desired density.

Fourier Transform Near-Infrared (FT-NIR) Spectroscopy

Fourier Transform Near-Infrared spectroscopy (FT-NIR) is a fiber optic, probe technology that measures the interactions (absorption and transmission) between light from the infrared region and matter. These interactions may be used to assess chemical composition. However, purely physical interactions, like forward and back scattering, can also be measured, and these interactions afford information about the relative size of any heterogeneous phases present, such as bubbles or particles.

FT-NIR spectroscopy has a much higher resolution and accuracy level than Near Infrared (NIR) spectrometers. The FT-NIR spectrometer has a spectral resolution of 0.3 nm (2 $cm^{-1}$ at 8000 $cm^{-1}$) whereas other grating or filter instruments are between 2 nm (5 $cm^{-1}$ at 5000 $cm^{-1}$) to 10 nm (25 $cm^{-1}$ at 5000 $cm^{-1}$). Further, dispersive instruments operate in a frequency domain whereas the Fourier Transformed NIR Infrared (FT-NIR) may be operated in the frequency domain or a time domain. The advantage of operating in a time domain allows for faster results. Near infrared wavelengths of light are absorbed by species due to distinctive molecular vibrations and low level electronic excitations. Many molecules have characteristic "fingerprint" absorption spectra in the near infrared.

While there is no exact definition of the frequency range related to the term "near infrared", generally, the term is used to define the range of frequencies between 4000 and 14000 $cm^{-1}$ (2.5 to 0.7 microns) wavenumber, and the technique of the present invention is applicable over this general range. However, preferably, the FT-NIR technique of the present invention is practiced within the range of 4300 to 9000 $cm^{-1}$ (2.2 to 1.1 microns), and even more preferably, the technique is practiced within the range of 5400 to 9000 $cm^{-1}$ (1.7 and 1.1 microns).

In use, the sample material is placed adjacent to the output of the interferometer and the detector. The sample absorbs radiation of specific wave lengths. The unabsorbed radiation is reflected (or otherwise transmitted) back to the detector and recorded as an interferogram. The interferogram is then transformed into a single channel spectrum by Fourier Transformation. The background spectrum is then used to calculate the transmission or absorption of the sample. After an interferogram has been collected, a computer performs a Fast Fourier Transform (FFT), which results in a frequency domain trace (i.e. intensity vs wavenumber). The detector used in an FT-NIR instrument must respond quickly because intensity changes are rapid (the moving mirror moves quickly). To achieve a good signal to noise ratio, many interferograms are obtained and then averaged.

The spectral range of the FT-NIR spectrum acquired is not particularly limited, but a useful range is generally from about 4000 $cm^{-1}$ to about 12000 $cm^{-1}$. It should be appreciated that useful spectral information is present in lower and higher frequency regions. Conversely, the spectral region acquired can be less than all of the 4000 $cm^{-1}$ to 12000 $cm^{-1}$ region. For many polyolefins, the majority of spectral intensity will be present in a region from about 6000 $cm^{-1}$ to about 12000 $cm^{-1}$. The region acquired can also include a plurality of sub-regions that need not be contiguous.

The frequency spacing of acquired data can be readily determined by one skilled in the art, based on considerations of machine resolution and capacity, acquisition time, data analysis time, and information density. Similarly, the amount of signal averaging used is readily determined by one skilled in the art based on machine and process efficiencies and limitations.

FT-NIR Equipment

A Bruker MATRIX-I FT-NIR spectrometer in combination with a standard computer can be used in diffuse reflectance mode to collect and analyze the spectra. The spectrometer has an internal light source, an interferometer, and a detector which measures, digitizes, and communicates the changes in spectral absorption or transmission between the sample spectra, the interferogram, and a reference spectra to the computer. The advantages of the FT-NIR technique are the higher resolution (4 $cm^{-1}$ across the entire range), higher signal-to-noise ratio, and the ability to measure all wavelengths of the spectra at once. The full range is between 3,800 and 12,000 $cm^{-1}$ and, the accuracy is +/−0.03 $cm^{-1}$. Output from the interferometer can be transmitted to the sample through a local aperture or through a fiber optic cable and probe, and the detector may be placed at any angle incident to the interferogram. When using fiber optic probes, the detector itself may be placed in a remote location, while the fiber optics are run between the detector and the reactor. The terminus of the fiber optics, a fiber optic probe, may be placed anywhere in the process where particle size is of interest. These may include the reactor bed, the recycle loop, or any sections of the product discharge system.

PCA/LWR Analysis

The FT-NIR spectrum includes information directly or indirectly related to various properties of the polyolefin sample. Conventionally, sample components are identified by the presence of unique spectral signatures, such as particular bands recognized as being due to particular vibrational modes of a molecule. Quantitative information such as concentration can then be obtained about a sample component by, for example, integrating the area under a particular peak and comparing the area to a calibration sample, by monitoring scattered intensity at a particular peak as a function of time, etc. In contrast to these conventional approaches, the present inventors have surprisingly found that particle properties can be determined from FT-NIR spectra without the need to identify or select particular spectral features, by using a multivariate model to correlate polymer properties with FT-NIR data. The model uses large, contiguous regions of the spectrum, rather than discrete spectral bands, thereby capturing large amounts of information density unavailable and unrecognized in conventional analysis.

In one embodiment, the data analysis described below is used to build and apply a predictive model for at least one property of the polyolefin particles selected from average particle size and particle size distribution.

Methods of the invention include obtaining a regression model for determining a polymer particle property, the regression model including principal component loadings and principal component scores; acquiring a FT-NIR spectrum of a polyolefin sample; calculating a new principal component score from at least a portion of the FT-NIR spectrum and the principal component loadings; and calculating the polymer particle property by applying the new principal component score to the regression model.

The regression model is preferably a locally weighted regression (LWR) model, using principal component analysis (PCA) eigenvectors. PCA is a well-known analytical method, and is described, for example, in Pirouette™ Multivariate Data Analysis for Windows software manual, Infometrix, Inc, Woodinville, Wash. (1985-2000), PLS_Toolbox™ software manual, Eigenvector Research, Inc., Manson, Wash. (1998), and references cited therein. LWR is described, for example, in Naes and Isaksson, *Analytical Chemistry*, 62, 664-673 (1990), Sekulic et al., *Analytical Chemistry*, 65, 835A-845A (1993), and references cited therein.

Principal Components Analysis is a mathematical method which forms linear combinations of raw variables to construct a set of mutually orthogonal eigenvectors (principal component loadings). Since the eigenvectors are mutually orthogonal, these new variables are uncorrelated. Further, PCA can calculate the eigenvectors in order of decreasing variance. Although the analysis computes a number of eigenvectors equal to the number of original variables, in practice, the first few eigenvectors capture a large amount of the sample variance. Thus, only a relatively small number of eigenvectors is needed to adequately capture the variance, and a large number of eigenvectors capturing minimal variance can be disregarded, if desired.

The data are expressed in an m (row) by n (column) matrix X, with each sample being a row and each variable a column optionally mean centered, autoscaled, scaled by another function or not scaled. The covariance of the data matrix, cov(X), can be expressed as:

$$\text{cov}(X) = X^T X / (m-1)$$

where the superscript T indicates the transpose matrix. The PCA analysis decomposes the data matrix as a linear combination of principal component scores vectors $S_i$ and principal component loading vectors (eigenvectors) $L_i$, as follows:

$$X = S_1 L_1^T + S_2 L_2^T + S_3 L_2^T + \ldots$$

The eigenvectors $L_i$ are eigenvectors of the covariance matrix, with the corresponding eigenvalues $\lambda_i$ indicating the relative amount of covariance captured by each eigenvector. Thus, the linear combination can be truncated after the sum of the remaining eigenvalues reaches an acceptably small value.

A model can be constructed correlating the intensity with a polymer property in PCA space using various linear or non-linear mathematical models, such as principal components regression (PCR), partial least squares (PLS), projection pursuit regression (PPR), alternating conditional expectations (ACE), multivariate adaptive regression splines (MARS), and neural networks (NN), to name a few.

In a particular embodiment, the model is a locally weighted regression model. Locally Weighted Regression (LWR) assumes that a smooth non-linear function can be approximated by a linear or relatively simple non-linear (such as quadratic) function, with only the closest data points being used in the regression. The q closest points are used and are weighted by proximity, and the regression model is applied to the locally weighted values.

In the calibration phase, FT-NIR spectra are acquired, and the polymer properties of the sample are measured in the laboratory, including average particle size and particle size distribution. For a desired polymer property, the data set including the measured polymer properties the samples and the FT-NIR spectral data for the samples is decomposed into PCA space to obtain a calibration data set. No particular number of calibration samples is required. One skilled in the art can determine the appropriate number of calibration samples based on the performance of the model and the incremental change in performance with additional calibration data. Similarly, there is no particular number of PCA eigenvectors required, and one skilled in the art can choose an appropriate number based on the amount of variance captured a selected number of eigenvectors and the incremental effect of additional eigenvectors.

The LWR model can be validated using methods known in the art. It is convenient to divide the calibration samples into two sets: a calibration data set, and a validation data set. The calibration data set is used to develop the model, and to predict the appropriate polymer property for the samples in the validation data set, using the validation data set FT-NIR spectra. Since the chosen polymer property for the validation data set samples is both calculated and measured, the effectiveness of the model can be evaluated by comparing the calculated and measured values.

The validated model can then be applied to sample spectra to predict the desired polymer property or properties.

If desired, a single model can be used to predict two or more polymer properties. Preferably, separate models are developed for each polymer property. Thus, in one embodiment, the present invention includes: obtaining a first regression model for determining a first polymer property, the first regression model including first principal component loadings and first principal component scores; obtaining a second regression model for determining a second polymer property, the second regression model including second principal component loadings and second principal component scores; acquiring a FT-NIR spectrum of a sample comprising polyolefin; calculating a new first principal component score from at least a portion of the FT-NIR spectrum and the first principal component loadings; calculating a new second principal component score from at least a portion of the FT-NIR spectrum and the second principal component loadings; calculating the first polymer property by applying the new first principal component score to the first regression model; and calculating the second polymer property by applying the new second principal component score to the second regression model.

Of course, more than two polymer properties can be determined by including third or more regression models. Advantageously, multiple polymer properties can be determined essentially simultaneously by using the same FT-NIR spectrum and applying several regression models to the spectral data.

In an embodiment, this invention relates to a method for the determination of the average particle size or particle size distribution of a material in a gas phase reactor comprising:
a) analyzing the average particle size and particle size distribution of a baseline composition using the method described in ASTM D1921;
b) analyzing the average particle size and particle size distribution of said baseline composition using a Fourier Transform-Near Infrared, FT-NIR, analysis technique;
c) preparing a calibration matrix by comparing results from said reference analytical technique of step a) to the results from said FT-NIR analysis technique of step b);
d) analyzing the material using an FT-NIR technique; and
e) identifying and quantifying the type and content of particles present in the material by comparing spectral data obtained from said FT-NIR technique of the material to said calibration matrix.

In a preferred embodiment of the invention, the calibration matrix is prepared using a technique based on data obtained by sieve analysis and FT-NIR analysis of selected baseline materials.

In a preferred embodiment of the invention, calibration matrix is based on a statistical analysis of FT-NIR spectral data and sieve analysis data obtained from the analysis of said baseline composition.

In a preferred embodiment of the invention, statistical analysis involves multiple linear regression (MLR), principal component regression (PCR), or partial least squares regression (PLSR).

In a preferred embodiment of the invention, FT-NIR technique uses a near-infrared region of the spectrum that has a frequency range of from between 4000 cm$^{-1}$ (2.5 microns) and 1000 cm$^{-1}$ (0.7 microns) wavenumber.

In a preferred embodiment of the invention, FT-NIR technique for analyzing said material is based on a reflective technique, transmission technique and/or transflectance technique.

Reaction Control

In one embodiment, the calculated polymer property is compared to a target polymer property, and at least one reactor parameter is adjusted based on the deviation between the calculated and target polymer property. The at least one reactor parameter can include the amounts of monomer, comonomer, catalyst and cocatalyst, the operating temperature of the reactor, the ratio of comonomer(s) to monomer, the ratio of hydrogen to monomer or comonomer, and other parameters that affect the chosen polymer property. For example, if the chosen polymer property is average particle size and the average particle size calculated from the PCA/LWR model is lower than a target average particle size, a reactor parameter can be adjusted to increase average particle size, such as, for example, increasing the residence time in the reactor.

It will be understood by those skilled in the art that other reactor constituent properties and other reactor parameters can be used. In a similar way as described above, the final polymer properties may be achieved by controlled metering reactor parameters in response to data generated by the average particle size analyzer.

In an embodiment, this invention relates to a process for determining polymer properties (such as particle size, average particle size, particle size distribution, and functions thereof) in a polymerization reactor system (preferably a gas phase polymerization reactor), the process comprising:
(a) obtaining a regression model for determining a polymer property (such as particle size, average particle size, particle size distribution, and functions thereof), the regression model including principal component loadings and principal component scores;
(b) acquiring a FT-NIR spectrum of a sample comprising polyolefin;
(c) calculating a new principal component score from at least a portion of the FT-NIR spectrum and the principal component loadings; and
(d) calculating the polymer property by applying the new principal component score to the regression model.

In a preferred embodiment of the invention step (a) comprises:
(i) obtaining a plurality of FT-NIR spectra of samples comprising polyolefins;
(ii) calculating principal component loadings and principal component scores from the spectra obtained in (i) using principal component analysis (PCA); and
(iii) forming the regression model using the principal component scores calculated in (ii) such that the regression model correlates the polymer property to the principal component scores.

In a preferred embodiment of the invention, the regression model is a locally weighted regression model.

In a preferred embodiment of the invention, the polymer property in the process described above is selected from particle size, average particle size, particle size distribution, and functions thereof.

In a preferred embodiment of the invention, the sample of step (b) comprises polyolefin particles.

In a preferred embodiment of the invention, the sample of step (b) comprises polyolefin particles and the step of acquiring a FT-NIR spectrum comprises:
(i) providing the sample of polyolefin particles; and
(ii) irradiating the sample and collecting scattered radiation during a sampling interval using a sampling probe, wherein there is relative motion between the sample and the sampling probe during at least a portion of the sampling interval.

In a preferred embodiment of the invention, the polymerization reactor is a gas phase reactor, preferably a fluidized-bed reactor.

In a preferred embodiment of the invention, the processes described above further comprise:
(i) obtaining a second regression model for determining a second polymer property, the second regression model including second principal component loadings and second principal component scores;
(ii) calculating a new second principal component score from at least a portion of the FT-NIR spectrum and the second principal component loadings; and
(iii) calculating the second polymer property by applying the new second principal component score to the second regression model.

In a preferred embodiment of the invention, this invention further relates to a process for determining polymer properties in a fluidized-bed reactor system, the process comprising:
(a) obtaining a locally weighted regression model for determining a polymer property selected from particle size, average particle size, particle size distribution, and functions thereof, the locally weighted regression model including principal component loadings and principal component scores;
(b) acquiring a FT-NIR spectrum of a sample comprising polyolefin particles;
(c) calculating a new principal component score from at least a portion of the FT-NIR spectrum and the principal component loadings; and
(d) calculating the polymer property by applying the new principal component score to the locally weighted regression model.

In a preferred embodiment of the invention, in the process for determining polymer properties in a fluidized-bed reactor system, the step of obtaining a regression model comprises:
(i) obtaining a plurality of FT-NIR spectra of samples comprising polyolefins;
(ii) calculating principal component loadings and principal component scores from the spectra obtained in (i) using principal component analysis (PCA); and
(iii) forming the regression model using the principal component scores calculated in (ii) such that the regression model correlates the polymer property to the principal component scores.

In a preferred embodiment of the invention, in the process for determining polymer properties in a fluidized-bed reactor system, the step of acquiring a FT-NIR spectrum comprises:
(i) providing the sample of polyolefin particles; and
(ii) irradiating the sample and collecting scattered radiation during a sampling interval using a sampling probe, wherein there is relative motion between the sample and the sampling probe during at least a portion of the sampling interval.

In a preferred embodiment of the invention, in the process for determining polymer properties in a fluidized-bed reactor system, further comprises:
(i) obtaining a second regression model for determining a second polymer property, the second regression model including second principal component loadings and second principal component scores;
(ii) calculating a new second principal component score from at least a portion of the FT-NIR spectrum and the second principal component loadings; and
(iii) calculating the second polymer property by applying the new second principal component score to the second regression model.

In a preferred embodiment of the invention, this invention relates to a process for controlling polymer properties in a polymerization reactor system, the process comprising:
(a) obtaining a regression model for determining a polymer property, the regression model including principal component loadings and principal component scores;
(b) acquiring a FT-NIR spectrum of a sample comprising polyolefin;
(c) calculating a new principal component score from at least a portion of the FT-NIR spectrum and the principal component loadings;
(d) calculating the polymer property by applying the new principal component score to the regression model; and
(e) adjusting at least one polymerization parameter based on the calculated polymer property.

EXPERIMENTAL

The FT-NIR was performed according to the following procedure: Polymer granules of interest were loaded into sample vials with consideration given to maintaining at least a one inch depth of polymer so as to maximize the amount of light reflected back to the detector, and to minimize the amount of light lost through the sample. The vials were placed on the top aperture of the Bruker MATRIX-I™ FT-NIR spectrometer and scans were collected. The software provided with the Bruker MATRIX-I™ FT-NIR spectrometer saved the average of six scans per analysis, and a total of three analyses were run on each sample. The sample was shaken between each analysis to insure that entire sample was interpreted. The output of the software-reflectance as a function of wavenumber, was then exported to a third-party software, Minitab version 16, for regression analysis.

Average particle size and particle size distribution were determined according to ASTM D1921 Standard Test Methods for Particle Size (Sieve Analysis) of Plastic Materials.

Polymer A is a metallocene ethylene-hexene copolymer having a 0.918 g/cc density, a 1.0 dg/min melt index, and a 120° C. melting point.

Polymer B is a metallocene ethylene-hexene copolymer having a 0.918 g/cc density, a 2.0 dg/min melt index, and a 118° C. melting point.

Polymer C is Ziegler-Natta (MCat™) ethylene-hexene copolymer having a density of 0.918 g/cc and 2.0 dg/min melt index, and a 120° C. melting point.

Example 1

Figure 2:
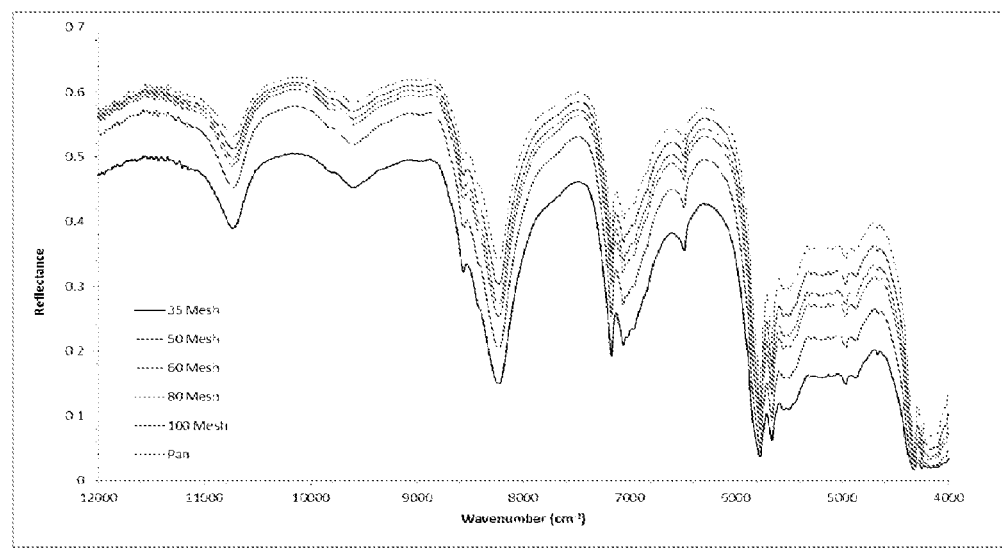
FIG. 2 is an FT-NIR spectra of an ethylene copolymer that has been separated into six sieved samples (the spectra from top to bottom are Pan, 100 Mesh, 80 Mesh, 60 Mesh, 50 Mesh, and 35 Mesh).

Reactor granules of Polymer A were sieved to obtain roughly 100 grams of each of seven sieve fractions (35, 58, 60, 80, 100, 120, and 200 Mesh). FT-NIR spectra were then obtained for some of the sieve samples and appear in FIG. 2. From the figure it can be observed that the spectra shift to higher reflectance in a systematic way, as the particles decrease in size. This is an indirect measurement of average particle size, and the average particle size of an unknown sample was inferred by comparing it to the spectra of these known particle sizes.

Since the smaller particle sizes are of more interest, some of the sieved samples is obtained above were resubmitted for further sieve analysis to assess the amount of polymer within each sieve fraction. This data is reported in Table A below as the percentage of polymer, or the frequency, that fell within different Mesh sizes and totals to 100%.

TABLE A

| Sieve Fraction | 10 Mesh | 14 Mesh | 18 Mesh | 25 Mesh | 35 Mesh | 45 Mesh |
|---|---|---|---|---|---|---|
| 35 | 0.4558 | 6.8935 | 24.969 | 23.9511 | 24.9322 | 11.9723 |
| 58 | 0 | 0 | 0 | 16.4364 | 27.6082 | 39.9945 |
| 60 | 0 | 0 | 0 | 0 | 0 | 11.7595 |
| 80 | 0 | 0 | 0 | 0 | 0 | 3.0036 |
| 100 | 0 | 0 | 0 | 0 | 0 | 0 |

TABLE A-continued

| | | | | | | |
|---|---|---|---|---|---|---|
| 120 | 0 | 0 | 0 | 0 | 0 | 0 |
| 200 | 0 | 0 | 0 | 0 | 0 | 0 |

| Sieve Fraction | 58 Mesh | 80 Mesh | 120 Mesh | 170 Mesh | 230 Mesh | Pan | Sum |
|---|---|---|---|---|---|---|---|
| 35 | 4.4411 | 1.6018 | 0.2972 | 0.2777 | 0.1157 | 0.0926 | 100 |
| 58 | 12.2272 | 3.0153 | 0.4564 | 0.1502 | 0.0621 | 0.0497 | 100 |
| 60 | 43.2397 | 33.9867 | 8.0374 | 0.7158 | 0.3968 | 1.8641 | 100 |
| 80 | 21.2955 | 57.1772 | 15.4948 | 0.9099 | 0.4631 | 1.6558 | 99.9999 |
| 100 | 3.6977 | 37.0888 | 51.7763 | 3.7158 | 2.0144 | 1.7068 | 99.9998 |
| 120 | 1.0825 | 21.4065 | 69.0683 | 5.1968 | 1.8733 | 1.3726 | 100 |
| 200 | 1.2453 | 6.7363 | 44.4502 | 17.2087 | 20.1933 | 10.1663 | 100.0001 |

Figure 3:
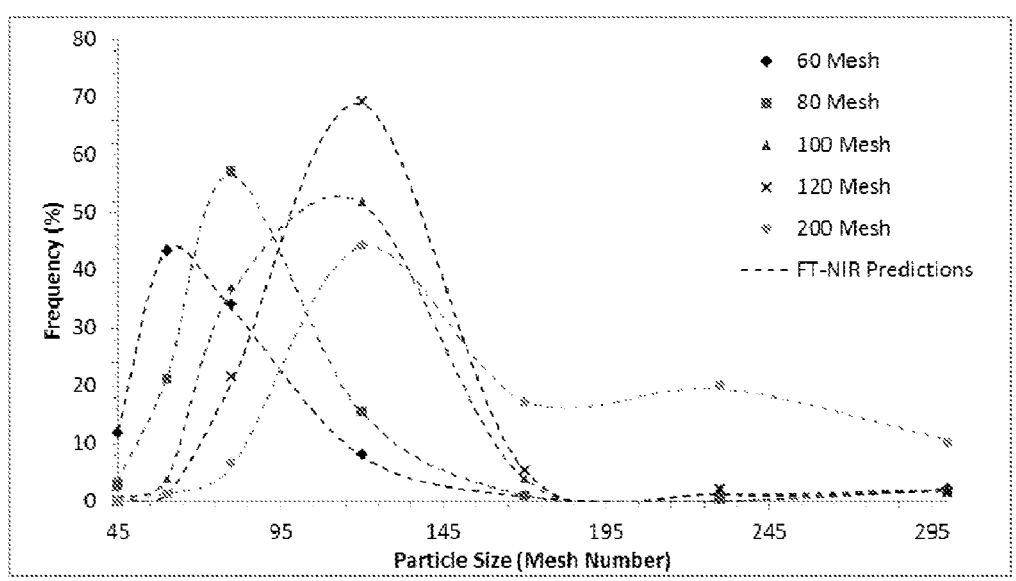
FIG. 3 is a graph of the predictions of the sieve analysis of various mesh sizes for the training set.
Figure 4:
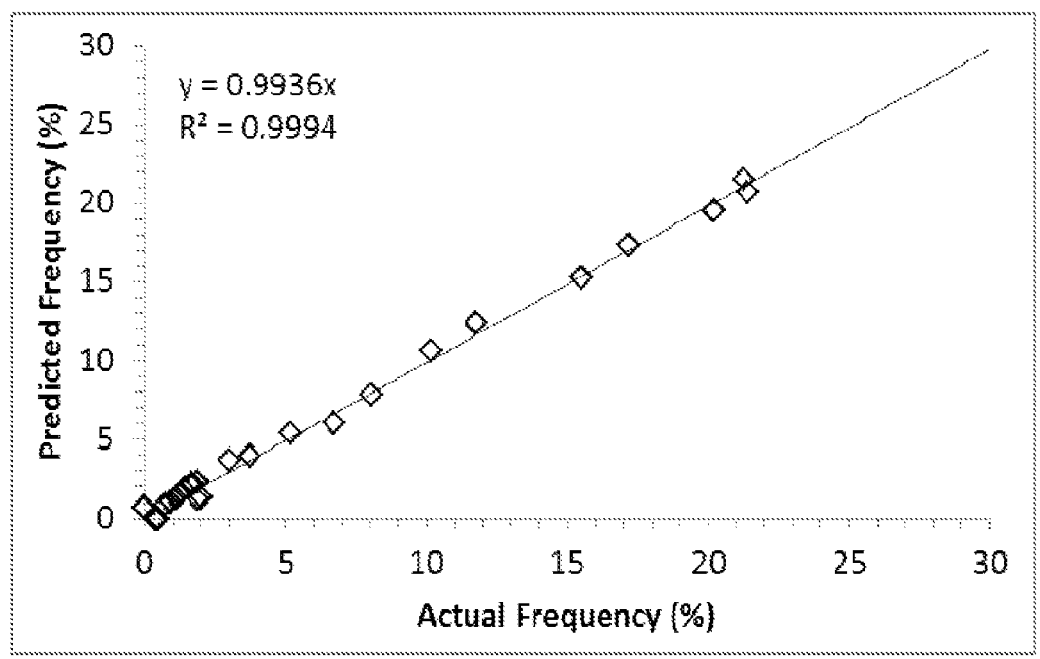
FIG. 4 is a graph of the predicted versus actual frequencies of the sieve analysis for the training set.
Figure 5:
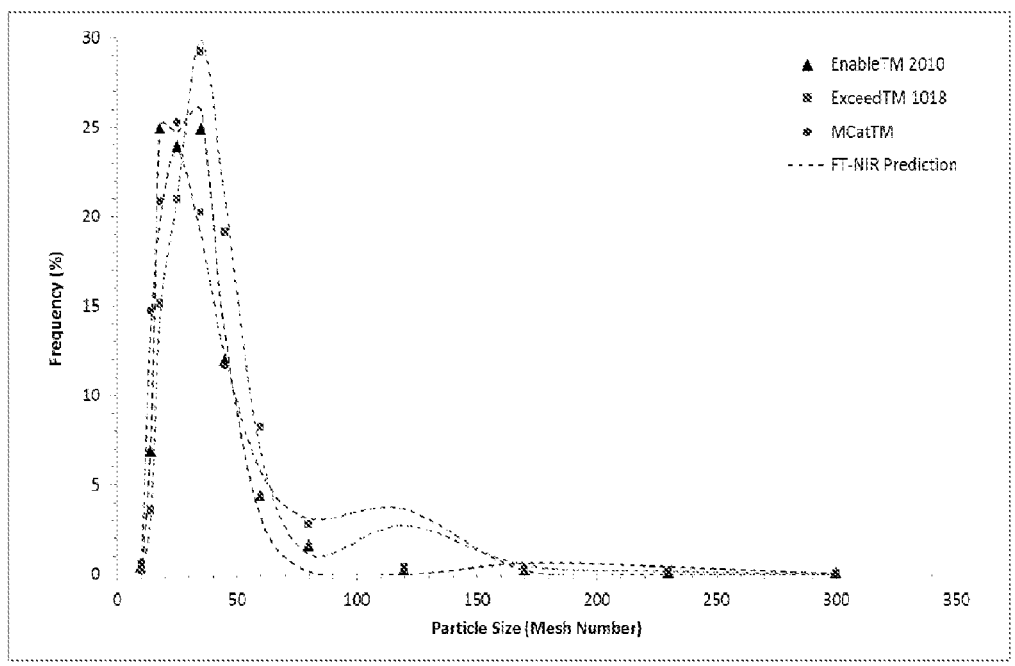
FIG. 5 is a graph of the predictions of the sieve analysis of the mesh sizes for the unknowns.
Figure 6:
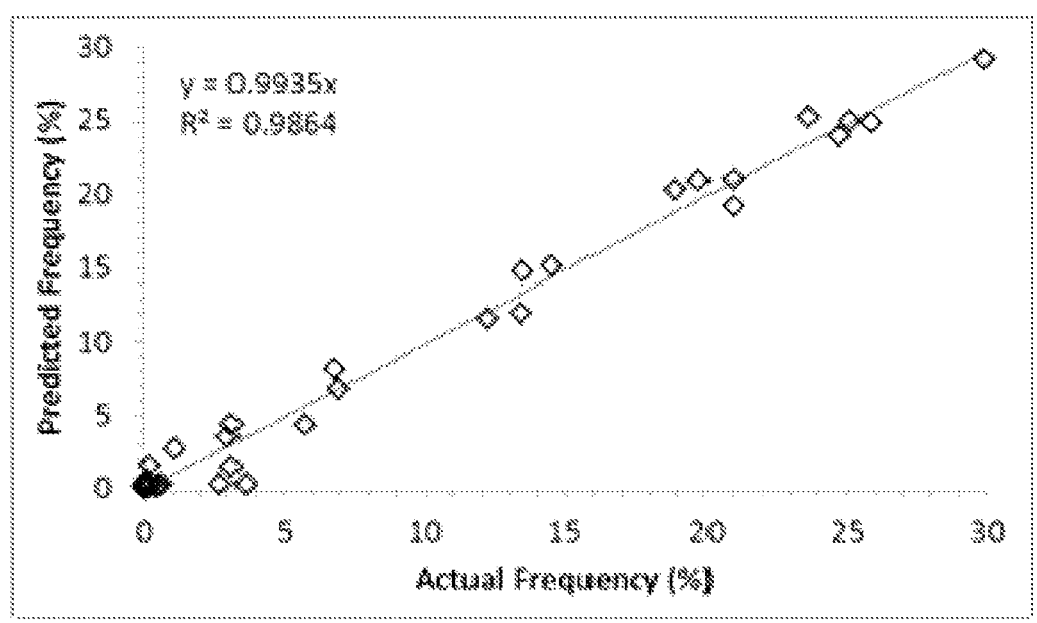
FIG. 6 is a graph of the predicted versus actual frequencies of the sieve analysis for unknowns.

These wavenumbers were then correlated using linear regression in Minitab Version 16 to the measured reflectance of the same sieve sample at various wavenumbers across the spectra. The wavenumbers used in this example are 10791, 9677, 8269, 7547, 6360, and 5249 cm$^{-1}$. This creates a relationship between the spectral reflectance value at a given wavenumber and the frequency at a given Mesh size. The results of these regressions are presented in FIGS. 3 and 4. Finally, these correlations were used to predict the frequencies at specified Mesh sizes for unknown reactor samples, based upon their FT-NIR spectra and the values of the reflectance at above-mentioned wavenumbers. The reactor samples were Polymer A, Polymer B and Polymer C, Exceed™ 1018, Enable™ 2010, and MCat™. The results of these predictions appear in FIGS. 5 and 6, and they show that with minimal training the FT-NIR spectral scans are capable of predicting the entire particle size distribution.

This methodology demonstrates a means for predicting the average particle size and particle size distribution from available FT-NIR spectral scans gathered in reflectance mode. This method can be implemented online using a fiber optic probe to measure the particle size in a gas phase reactor in-situ, in real time.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including". Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa, for example, the term "comprising" encompasses the terms "consisting essentially of," "is," and "consisting of" and anyplace "comprising" is used "consisting essentially of," "is," or "consisting of" may be substituted therefor.

I claim:

1. A method for the determination of the average particle size or particle size distribution of a material in a gas phase reactor comprising:
   a) determining a baseline composition, then analyzing the average particle size and particle size distribution of the baseline composition using the method described in ASTM D1921;
   b) analyzing the average particle size and particle size distribution of said baseline composition using a Fourier Transform-Near Infrared, FT-NIR, analysis technique;
   c) preparing a calibration matrix by comparing results from said reference analytical technique from step a) to the results from said FT-NIR analysis technique from step b);
   d) analyzing the material using an FT-NIR technique; and
   e) identifying and quantifying the type and content of particles present in the material by comparing spectral data obtained from said FT-NIR technique of the material to said calibration matrix.

2. The method of claim 1 wherein said FT-NIR technique uses a near-infrared region of the spectrum that has a frequency range of from between 4000 cm$^{-1}$ (2.5 microns) and 10,000 cm$^{-1}$ (1 micron) wavenumber.

3. The method of claim 1, wherein the sample comprises polyolefin particles.

4. The method of claim 1 wherein said FT-NIR technique for analyzing said material is based on a reflective technique, transmission technique and/or transflectance technique.

5. A method for the determination of the average particle size or particle size distribution of a material in a gas phase reactor comprising:
   a) selectin a baseline composition, then analyzing the average particle size and particle size distribution of the baseline composition using the method described in ASTM D1921;
   b) analyzing the average particle size and particle size distribution of said baseline composition using a Fourier Transform-Near Infrared, FT-NIR analysis technique;
   c) preparing a calibration matrix by comparing results from said reference analytical technique from step a) to the results from said FT-NIR analysis technique from step b);
   d) analyzing the material using an FT-NIR technique; and
   e) identifying and quantifying the type and content of particles present in the material by comparing spectral data obtained from said FT-NIR technique of the material to said calibration matrix, wherein said calibration matrix is prepared using a technique based on data obtained by sieve analysis and FT-NIR analysis of selected baseline materials.

6. The method of claim 5 wherein said calibration matrix is based on a statistical analysis of FT-NIR spectral data and sieve analysis data obtained from the analysis of said baseline composition.

7. The method of claim 6 wherein said statistical analysis involves multiple linear regression (MLR), principal component regression (PCR), or partial least squares regression (PLSR).

8. A process for determining polymer properties in a polymerization reactor system, the process comprising:
  (a) obtaining a regression model for determining a polymer property, the regression model including principal component loadings and principal component scores;
  (b) acquiring a FT-NIR spectrum of a sample comprising polyolefin;
  (c) calculating a new principal component score from at least a portion of the FT-NIR spectrum and the principal component loadings; and
  (d) calculating the polymer property by applying the new principal component score to the regression model.

9. The process of claim 8, wherein the step of obtaining a regression model comprises:
  (i) obtaining a plurality of FT-NIR spectra of samples comprising polyolefins;
  (ii) calculating principal component loadings and principal component scores from the spectra obtained in (i) using principal component analysis (PCA); and
  (iii) forming the regression model using the principal component scores calculated in (ii) such that the regression model correlates the polymer property to the principal component scores.

10. The process of claim 8, wherein the regression model is a locally weighted regression model.

11. The process of claim 8, wherein the polymer property is selected from particle size, average particle size, particle size distribution, and functions thereof.

12. The process of claim 8, wherein the sample comprises polyolefin particles.

13. The process of claim 12, wherein the step of acquiring a FT-NIR spectrum comprises:
  (i) providing the sample of polyolefin particles; and
  (ii) irradiating the sample and collecting scattered radiation during a sampling interval using a sampling probe,
  wherein there is relative motion between the sample and the sampling probe during at least a portion of the sampling interval.

14. The process of claim 8, wherein the polymerization reactor is a fluidized-bed reactor.

15. The process of claim 8, further comprising:
  (i) obtaining a second regression model for determining a second polymer property, the second regression model including second principal component loadings and second principal component scores;
  (ii) calculating a new second principal component score from at least a portion of the FT-NIR spectrum and the second principal component loadings; and
  (iii) calculating the second polymer property by applying the new second principal component score to the second regression model.

16. A process for determining polymer properties in a fluidized-bed reactor system, the process comprising:
  (a) obtaining a locally weighted regression model for determining a polymer property selected from particle size, average particle size, particle size distribution, and functions thereof, the locally weighted regression model including principal component loadings and principal component scores;
  (b) acquiring a FT-NIR spectrum of a sample comprising polyolefin particles;
  (c) calculating a new principal component score from at least a portion of the FT-NIR spectrum and the principal component loadings; and
  (d) calculating the polymer property by applying the new principal component score to the locally weighted regression model.

17. The process of claim 16, wherein the step of obtaining a regression model comprises:
  (i) obtaining a plurality of FT-NIR spectra of samples comprising polyolefins;
  (ii) calculating principal component loadings and principal component scores from the spectra obtained in (i) using principal component analysis (PCA); and
  (iii) forming the regression model using the principal component scores calculated in (ii) such that the regression model correlates the polymer property to the principal component scores.

18. The process of claim 16, wherein the step of acquiring a FT-NIR spectrum comprises:
  (i) providing the sample of polyolefin particles; and
  (ii) irradiating the sample and collecting scattered radiation during a sampling interval using a sampling probe,
  wherein there is relative motion between the sample and the sampling probe during at least a portion of the sampling interval.

19. The process of claim 16, further comprising:
  (i) obtaining a second regression model for determining a second polymer property, the second regression model including second principal component loadings and second principal component scores;
  (ii) calculating a new second principal component score from at least a portion of the FT-NIR spectrum and the second principal component loadings; and
  (iii) calculating the second polymer property by applying the new second principal component score to the second regression model.

20. A process for controlling polymer properties in a polymerization reactor system, the process comprising:
  (a) obtaining a regression model for determining a polymer property, the regression model including principal component loadings and principal component scores;
  (b) acquiring a FT-NIR spectrum of a sample comprising polyolefin;
  (c) calculating a new principal component score from at least a portion of the FT-NIR spectrum and the principal component loadings;
  (d) calculating the polymer property by applying the new principal component score to the regression model; and
  (e) adjusting at least one polymerization parameter based on the calculated polymer property.

21. The process of claim 20, wherein the step of obtaining a regression model comprises:
  (i) obtaining a plurality of FT-NIR spectra of samples comprising polyolefins;
  (ii) calculating principal component loadings and principal component scores from the spectra obtained in (i) using principal component analysis (PCA); and
  (iii) forming the regression model using the principal component scores calculated in (ii) such that the regression model correlates the polymer property to the principal component scores.

22. The process of claim 20, wherein the regression model is a locally weighted regression model.

23. The process of claim 20, wherein the polymer property is selected from particle size, average particle size, particle size distribution, and functions thereof.

24. The process of claim 20, wherein the polymerization reactor is a fluidized-bed reactor.

* * * * *